United States Patent [19]

Ivanov et al.

[11] Patent Number: 4,797,494
[45] Date of Patent: Jan. 10, 1989

[54] CARBAMIC ACID DERIVATIVES AND METHOD FOR PREPARING SAME

[76] Inventors: Mikhail G. Ivanov, prospekt Tsiolkovskogo, 31, kv. 47; Veniamin G. Golov, prospekt Pobedy 3, kv. 11, both of Dzerzhinsk Gorkovskoi oblasti; Vladimir N. Kuzmin, ulitsa Dobroselskaya, 195-a, kv. 48; Aida I. Alyakrinskaya, ulitsa Voroshilova, 6, kv. 2, both of Vladimir; Roman Y. Mushy, Gvardeisky prospekt, 45, kv. 15; Alexei D. Kovalev, prospekt Kosmonavtov, 15, kv. 46, both of Severodonetsk Voroshilovgradskoi oblasti; Nadezhda V. Shutova, prospekt Leninskogo Komsomola, 42, kv. 103, Dzerzhinsk Gorkovskoi oblasti; Jury A. Rodionov, prospekt Tsiolkovskogo, 81, kv. 31, Dzerzhinsk Gorkovskoi oblasti; Igor I. Molev, ulitsa Griboedova, 36, kv. 22, Dzerzhinsk Gorkovskoi oblasti; Ljudmila S. Yakovleva, Balaklavsky prospekt, 20, korpus 1, kv. 52, Moscow; Vitaly B. Berezin, Ryazansky prospekt, 51, kv. 106, Moscow; Alexei I. Petrashko, ulitsa Tashkentskava, 24, korpus 1, kv. 181, Moscow; Gennady M. Shuev, ulitsa Prosojuznaya, 18, kv. 64; Boris A. Bukin, ulitsa Profsojuznaya, 40, kv. 17, both of Narofominsk Moskovskoi oblasti; Tamara M. Belkina, deceased, late of Moscow; by Naum S. Belkin, administrator, ulitsa Flotskaya, 18, kv. 94, Moscow, all of U.S.S.R.

[21] Appl. No.: 901,753

[22] Filed: Aug. 28, 1986

Related U.S. Application Data

[62] Division of Ser. No. 573,795, Jan. 25, 1984, Pat. No. 4,623,931.

[51] Int. Cl.$^4$ ............................................. C07D 231/10
[52] U.S. Cl. ....................................... 548/374; 548/378
[58] Field of Search ................................ 548/374, 378

[56] References Cited

U.S. PATENT DOCUMENTS 3,317,463  5/1967  Schonfeld et al. .................... 560/42
4,191,833  3/1980  Tucker .................................. 548/378

OTHER PUBLICATIONS

Morrison et al., Textbook "Organic Chemistry" 3rd Ed., Allyn and Bacon, Inc., Boston, MA 1978, p. 1044.

Primary Examiner—John M. Ford
Attorney, Agent, or Firm—Ladas & Parry

[57] ABSTRACT

Carbamic acid derivatives having the following general formula:

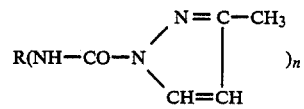

wherein R is an aromatic radical containing at least one benzene ring with at least one hydrogen atom substituted with a methyl, methylene or methine group; n=2 to 7.

A method for preparing carbamic acid derivatives which comprises reacting 3(5)-methylpyrazole with an isocyanate of the general formula: R(NCO)$_n$, wherein: R is an aromatic radical containing at least one benzene ring having at least one hydrogen atom substituted with a methyl, methylene or methine group; n=2 to 7; the reaction being conducted in a melt or a solution of an inert organic solvent.

4 Claims, No Drawings

CARBAMIC ACID DERIVATIVES AND METHOD FOR PREPARING SAME

This is a divisional of co-spending application Ser. No. 573,795 filed on Jan. 25, 1984, now U.S. Pat. No. 4,623,731.

FIELD OF THE INVENTION

The present invention relates to novel organic compounds and, more specifically, to carbamic acid derivatives.

The carbamic acid derivatives according to the present invention are useful as components of various polyurethane materials—adhesives, coatings, binders, as well as modifying additives to compositions employed in the production of other polymeric materials.

BACKGROUND OF THE INVENTION

Known in the art are carbamic acid derivatives of the general formula $R(NHCOOR')_n$, wherein R and R' are aromatic radicals, n is at least 2, which are useful in the application areas specified hereinabove (cf. J. H. Saunders, K. C. Frish Polyurethanes. Chemistry and Technology. Part I.Chemistry Interscience Publ., N.-Y.-London, 1962; U.S. Pat. No. 3,317,463 published 1967 Cl.260-47).

These compounds are prepared by reacting isocyanates with various substances containing reactive hydroxy groups, predominantly with phenol or substituted phenols.

When admixed to different diols or polyos, these compounds form compositions which are rather stable at normal temperatures. However, upon heating of such compositions destruction of carbamic acid derivatives occurs with liberation of isocyanates, wherefore they are referred to as blocked or masked isocyanates. The liberated isocyanates enter into reaction with diols or polyols of the composition to give a polyurethane polymer. The temperature at which an intensive decomposition of the carbamic acid derivatives occurs in contact with a hydroxyl compound is referred to as the exchange decomposition temperature. This temperature defines the curing temperature of compositions incorporating the above-specified compound.

The carbamic acid derivatives mentioned hereinbefore have a high exchange decomposition temperature (above 150° C.). This substantially limits opportunities for their application, for example as adhesives for the materials possessing no high thermal stability.

Furthermore, curing of a composition in this case is accompanied by evolution, into the environments, of vapours of a very toxic phenol formed upon decomposition of the above-mentioned compounds.

Known in the art are modes for lowering the exchange decomposition temperature of carbamic acid derivatives comprising isocyanates blocked by phenols through the addition, thereto, of quaternary ammonium bases and organo-tin compounds (cf. U.S. Pat. Nos. 3,668,186; 3,676,402; published 1972). These processes make it possible to slightly lower the exchange decomposition temperature of the above-indicated compounds, but they fail to eliminate the difficulties associated with evolution of strongly toxic phenol vapours into the environments upon curing of the composition.

OBJECT OF THE INVENTION

It is an object of the present invention to provide such carbamic acid derivatives being blocked isocyanates which would possess a lowered exchange decomposition temperature and would not evolve strongly toxic compounds into the environments in the stage of their application.

SUMMARY OF THE INVENTION

This object is accomplished by the provision of carbamic acid derivatives having the following general formula:

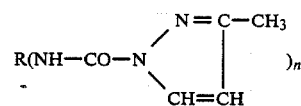

wherein R is an aromatic radical containing at least one benzene ring, where at least one atom of hydrogen is substituted with a methyl, methylene or methine group; n=2-7.

The thus-prepared carbamic acid derivatives, owing to the structure thereof, have a lowered exchange decomposition temperature which results in a decreased curing temperature of compositions based thereon. Furthermore, during the stage of curing of these compositions no vapours of strongly toxic substances are liberated into the ambient medium. Adhesive joints or coatings based on these derivatives possess improved physico-mechanical characteristics.

Carbamic acid derivatives according to the present invention correspond to the above-given general formula, wherein R is:

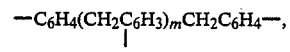

wherein m=0-3, n=m+2; $CH_2(C_6H_4)_2$ at n=2; $CH(C_6H_4)_3$ at n=3.

Such compounds are useful as curing agents for polyurethane adhesives and modifying additives.

Carbamic acid derivatives with the benzene ring of said radical, wherein one hydrogen atom is substituted with the atom of nitrogen of isocyanurate group, impart heat-resistance and high physico-mechanical properties to coatings based thereon. For this reason it is advisable to use a carbamic acid derivative, wherein the radical R has the meaning:

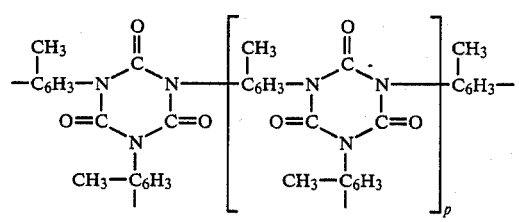

wherein p=0-4, n=p+3, in powder-like paints and in the manufacture of heat-resistant coatings. The present invention also covers carbamic acid derivatives with the benzene ring of said radical having one-hydrogen atom substituted with the atom of nitrogen of urethane group.

Carbamic acid derivatives, wherein R has the meaning: $NH(CONHCH_2CH_2OOCNHC_6H_4CH_2C_6H_4)_2$ at $n=2$;

$—C_6H_4CH_2C_6H_4NHCOO[CH_2CH_2COO(CH_2)_4COO]_gCH_2CH_2OOCNHC_6H_4CH_2—C_6H_4—$ at $g = 8-14$ $n = 2$;

can find a wide application as components of various adhesives, e.g. an adhesive employed in the manufacture of a filmsynthocardboard for insulation of electric motors.

The present invention also relates to a method for preparing carbamic acid derivatives of the above-given general formula which comprises reacting 3(5)-methylpyrazole with an isocyanate of the general formula: $R(NCO)_n$, wherein: R is an aromatic radical containing at least one benzene ring with at least one hydrogen atom being substituted with a methyl, methylene or methine group, $n=2$ to 7; the reaction being conducted in a melt or in a solution of an inert organic solvent.

The method according to the present invention is simple both as regards its scheme and the equipment employed. The reaction on which the present method is based is a reaction of an isocyanate with 3(5)-methylpyrazole which, at its high reactivity, is much less toxic than phenols. The use of 3(5)-methylpyrazole makes it possible to provide carbamic acid derivatives with such a structure which ensures a lowered temperature of an exchange decomposition thereof.

To improve quality of the desired product, it is advisable to use 1,2-dichloroethane, N,N-dimethylformamide, ethylacetate as the organic solvent.

To enlarge the scope of carbamic acid derivatives, it is advisable to use isocyanates wherein R has the following meanings:

$$—C_6H_4(CH_2C_6H_3)_mCH_2C_6H_4—$$

at $m=0-3$ and $n=m+2$; $CH_2(C_6H_4)_2$ at $n=2$; $CH(C_6H_4)_3$ at $n=3$.

In the case of using carbamic acid derivatives in paint and coating compositions, it is advisable to use, for their preparation, isocyanates having, in the benzene ring of the above-mentioned radical, one hydrogen atom substituted with an atom of nitrogen of isocyanurate group so that R can have the following meaning:

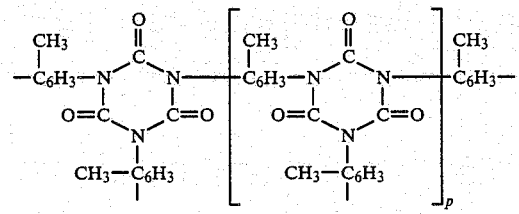

$p=0-4$, $n+p+3$.

To obtain carbamic acid derivatives useful in adhesive compositions, it is advisable to use isocyanates having, in the benzene ring of the above-mentioned radical, one hydrogen atom substituted with an atom of nitrogen of urethane group so that R can have the following meanings; $NH(CONHCH_2CH_2OOCNHC_6H_4CH_2C_6H_4)_2$ at $n=2$; $—C_6H_4CH_2C_6H_4NHCOO[CH_2CH_2COO(CH_2)_4COO]_gCH_2CH_2OOCNHC_6H_4—CH_2C_6H_4—$ at $g=8-14$, $n=2$;

$$C_2H_5C(CH_2OOCNHC_6H_3)_{\overline{3}} \text{ at } n = 3.$$
$$\phantom{C_2H_5C(}|\phantom{CH_2OOCNHC_6H_3)}$$
$$\phantom{C_2H_5C(}CH_3$$

DETAILED DESCRIPTION OF THE INVENTION

Carbamic acid derivatives prepared according to the present invention comprise, depending on a molecular mass thereof, solid or resinous substances. Their melting points vary within a rather wide range of from 90° to 160° C. The solubility of these compounds depends on the radical type and can vary, in N,N-dimethylformamide, from 4–5 to 50–55% by mass.

The exchange decomposition temperature of these carbamic acid derivatives vary within the range of from 100° to 155° C. depending on the radical type.

An increased molecular mass of the radical results, as a rule, in lowering of these temperatures.

Moreover, by changing the type of the radical R in carbamic acid derivatives, it is possible to derive certain advantages at the stage of their use. Thus, the use of a compound with R containing isocyanurate groups imparts good physico-mechanical properties to coatings obtained therefrom, wherefore it can be used in powder-like paints and in the manufacture of heat-resistant coatings.

The carbamic acid derivatives having R containing urethane groups in a mixture with epoxy resins possess good adhesive properties, a lowered curing temperature and a high flexibility of the adhesive joint, thus enabling their use for bonding film-like materials, for example in the manufacture of a filmsynthocardboard.

In IR-spectra of carbamic acid derivatives the band of isocyanate group ($\nu=2275$ cm$^{-1}$) is absent and bands with $\nu$ of 3370 to 3300 cm$^{-1}$, 1730–1700 and 1250–1230 cm$^{-1}$ appear which are characteristic of the group

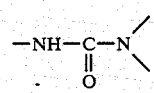

and absent in the starting compounds.

The method for preparing carbamic acid derivatives according to the present invention resides in reacting 3(5)-methylpyrazole with an isocyanate of the general formula: $R(NCO)_n$, wherein R is an aromatic radical containing at least one benzene ring with at least one hydrogen atom substituted with a methyl-, methylene or methine group; $n=2$ to 7.

This reaction can be conducted both in a melt and in a solvent which is inactive relative to the isocyanate.

In the case of carrying out the reaction in a melt the isocyanate is heated to a temperature exceeding its melting point and 3(5)-methylpyrazole is added under stirring. In doing so that reaction mass is heated due to the exothermal character of the reaction, whereafter the mass is gradually solidified. The resulting block is heated for 1-2 hours at a temperature of 80°-100° C. and disintegrated.

The reaction of an isocyanate with 3(5)-methylpyrazole should be conducted in an inert organic solvent with a view to a further application of the carbamic acid derivative in the form of a solution or in the case of using an isocyanate with a high melting point (above 80°-100° C.). In the latter case a high initial reaction temperature would cause local overheatings (up to 180°-200° C.) resulting in resinification of the isocyanate. It is advisable, accordingly, to use high-concentration (up to 75-85% by mass) solutions of an isocyanate which makes it possible to avoid a special stage of separation of the solvent, since the major portion thereof is distilled-off during the reaction.

The procedure of carrying out the reaction in a solvent does not substantially differ from that of the reaction conducted in a melt.

The use of 3(5)-methylpyrazole for the preparation of carbamic acid derivatives results, due to a high reactivity of this compound, in a simple process scheme (lack of catalysts, high temperatures, etc.); it does not necessitate the use of a sophisticated process equipment.

Carbamic acid derivatives prepared by the method according to the present invention feature of a lowered exchange decomposition temperature due to their structure. At the same time, processing of these derivatives is associated with a far lesser risk of poisoning of the operating personnel due to a lower toxicity and volatility of 3(5)-methylpyrazole as compared to phenol. The use of these derivatives in epoxy compositions makes it possible to reduce liberation of 3(5)-methylpyrazole into the environments, since in this case it reacts with epoxy groups.

Furthermore, the use of the carbamic acid derivatives according to the present invention in the majority of cases improves physico-mechanical characteristics of the materials produced therefrom.

For a better understanding of the present invention some specific examples illustrating particular carbamic acid derivatives are given hereinbelow.

EXAMPLE 1

200 g of a mixture of polyphenylenepolymethylenepolyisocyanates prepared by phosgenation of a product of condensation of aniline with formaldehyde are charged into a flask. The content of isocyanate groups in this mixture is 29.4% by mass. The product comprises a mixture of isocyanates of the general formula:

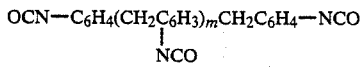

wherein m=0 to 3, with predomination of 4,4'-diphenylmethanediisocyanate therein (m=0).

The mixture is added with 119 g of 3(5)-methylpyrazole. During stirring the mixture gets warmed and solidified. The solid mass is heated for 2 hours at the temperature of 80° C., then cooled and disintegrated. The yield is quantitative.

The exchange decomposition temperature of the resulting product is 117° C.; for a similar isocyanate blocked by phenol it is equal to 150° C.

EXAMPLE 2

5.0 g of 4,4'-diphenylmethanediisocyanate are charged into a flask and 3.6 g of 3(5)-methylpyrazole are added thereto at the temperature of 50° C. under a vigorous stirring. During stirring the mixture gets heated and solidified.

The solid mass is heated for 2 hours at the temperature of 80° C., then cooled, disintegrated and recrystallized from hot dioxane to give 6.0 g of a product having its melting point of 134°-136° C. and the exchange decomposition temperature of 155° C. The product has the following elemental composition. Found: %: C 66.3, H 5.3, N 20.1. Calculated for $C_{23}H_{22}N_6O_2$, %: C 66.66, H 5.35, N 20.28, O 7.71. In the IR-spectrum of the product the band of the isocyanate group ($\nu 2275$ cm$^{-1}$) is absent and bands of 3370, 3350, 1730 and 1230 cm$^{-1}$ appear which are characteristic of the group

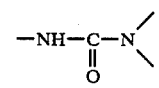

and absent in the initial compounds.

The exchange decomposition temperature of 4,4'-diphenylmethanediisocyanate blocked by phenol is 185° C.

EXAMPLE 3

1,000 g of a 20% solution of triphenylmethanetriisocyanate in 1,2-dichloroethane is placed into a distillation flask and 595 ml of the solvent are distilled-off at the still temperature of 130° C. Remained in the flask are 255 g of a mass liquid at room temperature and containing 26.6% by mass of isocyanate groups, which corresponds to the content of triphenylmethanetriisocyanate of 77.5% by mass in the solution, 139 g of 3(5)-methylpyrazole are added to the resulting mass at the temperature of 20° C. under vigorous stirring. The mixture becomes self heated to 130° C. boils and a portion of 1,2-dichloroethane is thus distilled-off. On cooling the reaction mixture solidifies. The yield is quantitative.

The exchange decomposition temperature of the thus-obtained product is 115°-120° C., while for a similar isocyanate but blocked with phenol it is equal to 170°-175° C.

EXAMPLE 4

Charged into the flask are 200 g of a preliminarily trimerized (in the presence of lithium acetate) 2,4-tolylenediisocyanate to the content of isocyanate groups of 26.0% by mass. The resulting isocyanate comprises substantially a prepolymer of the following formula:

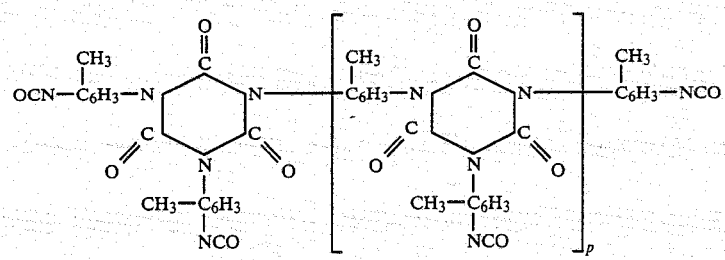

wherein p=0-4, n=p+3.

This isocyanate is added, under vigorous stirring at the temperature of 50° C., with 111 g of 3(5)-methylpyrazole. In the course of stirring the mixture is heated and solidified. The solid mass is heated for 2 hours at the temperature of 80° C., then cooled and disintegrated. The product is a substituted polyfunctional methylpyrazolylcarboxamide containing a polyisocyanurate based on 2,4-tolylenediisocyanate. As an impurity the product contains 9% of 2,4-bis-(3-methylpyrazolecarboxamido)-toluene. The product yield is quantitative.

The product has its exchange decomposition temperature of 115°–120° C.; that of a trimer of 2,4-tolylenediisocyanate blocked by phenol is 145°–150° C.

EXAMPLE 5

To a solution of 14 g of 4,4'-diphenylmethanediisocyanate containing, as an impurity, 1% by mass of 2,4'-diphenylmethanediisocyanate in 9.5 g of N,N-dimethylformamide a solution of 20 g of a polyesterdiol (polyethyleneglycol adipate containing 1.8% by mass of OH groups) in 9.5 g of dimethylformamide is added under stirring. The resulting mixture is added under stirring, with a solution of 3 g of a diol of the formula:

HOCH$_2$CH$_2$NHCONHCONHCH$_2$CH$_2$OH (a product of a thermal polycondensation of β-hydroxyethylurea) in 9.5 g of N,N-dimethylformamide. The mixture gets heated. When the content of NCO-groups in the mixture is made equal to 2.2% by mass, the product dissolved in N,N-dimethylformamide comprises substantially a mixture of two polymeric isocyanates of the following formulae:

NH(CONHCH$_2$CH$_2$OOCNHC$_6$H$_4$CH$_2$C$_6$H$_4$-NCO)$_2$

OCNC$_6$H$_4$CH$_2$C$_6$H$_4$NHCOO[CH$_2$CH$_2$COO(CH$_2$)$_4$COO]$_g$CH$_2$CH$_2$OOCNHC$_6$H$_4$CH$_2$C$_6$H$_4$NCO at g=8–14.

This mixture is added, under stirring with 2.8 g of 3(5) methylpyrazole. A very rapid reaction proceeds between isocyanate groups of the oligomer formed upon the reaction of the components and 3(5) methylpyrazole. The resulting product has the exchange decomposition temperature of 90°–100° C.

EXAMPLE 6

15 g of the polyesterdiol and 3 g of the diol employed in Example 5 hereinabove are dissolved in 28.5 g of N,N-dimethylformamide. The resulting solution is added, under stirring, with 14 g of a mixture of isomers of diphenylmethanediisocyanate containing 36.5% by mass of 4,4'-diphenylmethanediisocyanate, 62.2% by mass of 2,4'-diphenylmethanediisocyanate and 1.3% by mass of 2,2'-diphenylmethanediisocyanate. The weight ratio between diphenylmethanediisocyanate, polyesterdiol and diol is equal to 1:1.07:0.215. The mixture gets heated. On completion of the reaction the mixture is cooled to room temperature to give 58 g of a 55% solution of a polyesterurethane containing 3.4% by mass of NCO - groups and comprising a mixture of two polymeric isocyanates of the following formulae:

NH(CONHCH$_2$CH$_2$OOCNHC$_6$H$_4$CH$_2$C$_6$H$_4$-NCO)$_2$ and

OCNC$_6$H$_4$CH$_2$C$_6$H$_4$NHCOO(CH$_2$CH$_2$COO/CH$_2$/$_4$COO)$_g$CH$_2$CH$_2$OOCNHC$_6$-H$_4$—CH$_2$C$_6$H$_4$NCO at g=8 to 14.

The solution is added with 3.85 g of 3(5)-methylpyrazole under stirring. The product is thus obtained which is similar to that prepared in Example 5 hereinbefore.

EXAMPLE 7

Charged into a flask are 11.0 g of a 75% by mass solution of a product of interaction of 2,4-tolylenediisocyanate with trimethylolpropane in ethylacetate with the content of isocyanate groups in the solution of 14.2%.

The major portion of the product is constituted by tris(isocyanato-tolylcarbamate) of 1,1,1-trimethylolpropane. Then 3.1 g of 3(5)-methylpyrazole are introduced into the flask under vigorous stirring. In the course of stirring the mixture gets warmed-up and solidifies. The solid mass is heated for two hours at the temperature of 80° C., then cooled and disintegrated. The yield is quantitative. The exchange decomposition temperature of the thus-prepared compound is 95° C., while that of a similar product blocked by phenol is equal to 130° C.

What is claimed is:

1. A compound of the formula

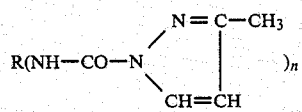

wherein R is selected from the group consisting of

NH(CONHCH$_2$CH$_2$OOCNHC$_6$H$_4$CH$_2$C$_6$H$_4$)$_2$ wherein n=2

C$_6$H$_4$CH$_2$C$_6$H$_4$NHCOO[CH$_2$CH$_2$COO(CH$_2$)$_4$COO]$_g$CH$_2$CH$_2$OOCNHC$_6$H$_4$CH$_2$—C$_6$H$_4$—, in which g=8–14 wherein n=2, and $$C_2H_5C(CH_2OOCNHC_6H_3)_3,$$
$$|$$
$$CH_3$$

wherein n=3.

2. A compound, as in claim 1 wherein R is $$NH(CONHCH_2CH_2OOCNHC_6H_4CH_2C_6H_4)_2$$

wherein n=2.

3. A compound, as in claim 2 wherein R is $$C_6H_4CH_2C_6H_4NHCOO[CH_2CH_2COO$$
$$(CH_2)_4COO]_gCH_2CH_2OOCNHC_6H_4CH_2-C_6-$$
$$H_4-,$$

in which g=8-14 wherein n=2.

4. A compound, as in claim 1 wherein R is $$C_2H_5C(CH_2OOCNHC_6H_3)_3,$$
$$|$$
$$CH_3$$

wherein n=3.

* * * * *